(12) United States Patent
Deadwyler et al.

(10) Patent No.: US 8,043,230 B2
(45) Date of Patent: Oct. 25, 2011

(54) URINE SPECIMEN COLLECTION DEVICE

(76) Inventors: Glynis Deadwyler, Cleveland Heights, OH (US); Sam Bigham, Oakwood Village, OH (US)

(*) Notice: Subject to any disclaimer, the term of this patent is extended or adjusted under 35 U.S.C. 154(b) by 20 days.

(21) Appl. No.: 11/625,312

(22) Filed: Jan. 20, 2007

(65) Prior Publication Data
US 2008/0177201 A1    Jul. 24, 2008

(51) Int. Cl.
A61B 5/00 (2006.01)
A65D 81/00 (2006.01)
A61M 1/00 (2006.01)
A61F 5/44 (2006.01)

(52) U.S. Cl. ........ 600/575; 600/573; 600/574; 604/327; 604/347

(58) Field of Classification Search .................. 600/573, 600/574, 575; 604/403, 327, 347; 73/149
See application file for complete search history.

(56) References Cited

U.S. PATENT DOCUMENTS

| | | | |
|---|---|---|---|
| 3,750,648 A * | 8/1973 | Gleason et al. | 600/574 |
| 3,967,645 A * | 7/1976 | Gregory | 137/846 |
| 4,265,118 A * | 5/1981 | Griesel | 73/427 |
| 4,276,889 A | 7/1981 | Kuntz et al. | |
| D264,248 S | 5/1982 | Steigerwald et al. | |
| 4,331,162 A | 5/1982 | Kuntz et al. | |
| 4,393,881 A | 7/1983 | Shah | |
| 4,423,741 A * | 1/1984 | Levy | 600/581 |
| 4,492,258 A | 1/1985 | Lichtenstein et al. | |
| 4,494,581 A | 1/1985 | Gordon | |
| 4,557,274 A | 12/1985 | Cawood | |
| 4,569,090 A | 2/1986 | Muller | |
| 4,753,249 A | 6/1988 | Muller | |
| 4,769,215 A | 9/1988 | Ehrenkranz | |
| 4,852,560 A | 8/1989 | Hermann, Jr. et al. | |
| 5,139,742 A * | 8/1992 | Heijink | 422/58 |
| 5,352,182 A * | 10/1994 | Kalb et al. | 600/30 |
| 5,409,473 A * | 4/1995 | Rosenshein | 604/329 |
| 5,476,434 A * | 12/1995 | Kalb et al. | 600/30 |
| 5,509,889 A * | 4/1996 | Kalb et al. | 600/30 |
| 5,518,003 A | 5/1996 | Allan | |
| 5,704,353 A * | 1/1998 | Kalb et al. | 600/342 |
| 5,711,310 A | 1/1998 | Vinayagamoorthy et al. | |
| 5,766,136 A | 6/1998 | Cawood | |
| D434,494 S | 11/2000 | Wilkinson et al. | |
| 7,213,272 B2 * | 5/2007 | Arguelles | 4/144.1 |
| 2001/0037098 A1 * | 11/2001 | Snyder | 604/331 |
| 2002/0193760 A1 * | 12/2002 | Thompson | 604/318 |
| 2003/0118255 A1 * | 6/2003 | Miller | 383/205 |
| 2003/0190259 A1 | 10/2003 | Alley | |

(Continued)

FOREIGN PATENT DOCUMENTS
WO    WO 9013280 A1 * 11/1990

*Primary Examiner* — Max Hindenburg
*Assistant Examiner* — Sean Dougherty
(74) *Attorney, Agent, or Firm* — Scott M. Oldham, Esq.; Hahn Loeser + Parks LLP

(57) ABSTRACT

A urine specimen collection device includes a body adapted to support a specimen collector. The device includes a pull tab movably connected to the body, the pull tab being movable between a first position and a second position. The urine selectively flows through the body and into the specimen collector when the pull tab is generally positioned in the second position and urine flows through the body and into a diverter tube when the pull tab is generally positioned in the first position.

15 Claims, 5 Drawing Sheets

U.S. PATENT DOCUMENTS

2004/0267159 A1 12/2004 Yong et al.
2005/0004493 A1 1/2005 Yong et al.
2005/0177070 A1* 8/2005 Levinson ...................... 600/574
2006/0064033 A1* 3/2006 Stewart et al. ................ 600/573
2007/0180928 A1* 8/2007 Newton .......................... 73/861
2007/0205054 A1* 9/2007 Gentles et al. ................ 182/230

* cited by examiner

URINE SPECIMEN COLLECTION DEVICE

BACKGROUND OF THE INVENTION

Urine specimen collection devices are important for the collection of urine for analysis. Midstream collection of urine can be challenging. Timing of positing a collection cup after the stream of urine has begun can require coordination and be unsanitary. Current attempts to make specimen collection devices for midstream collection have been largely unsuccessful. There remains a long-felt need for a specimen collection device for midstream urine collection.

SUMMARY OF INVENTION

Figure 1:
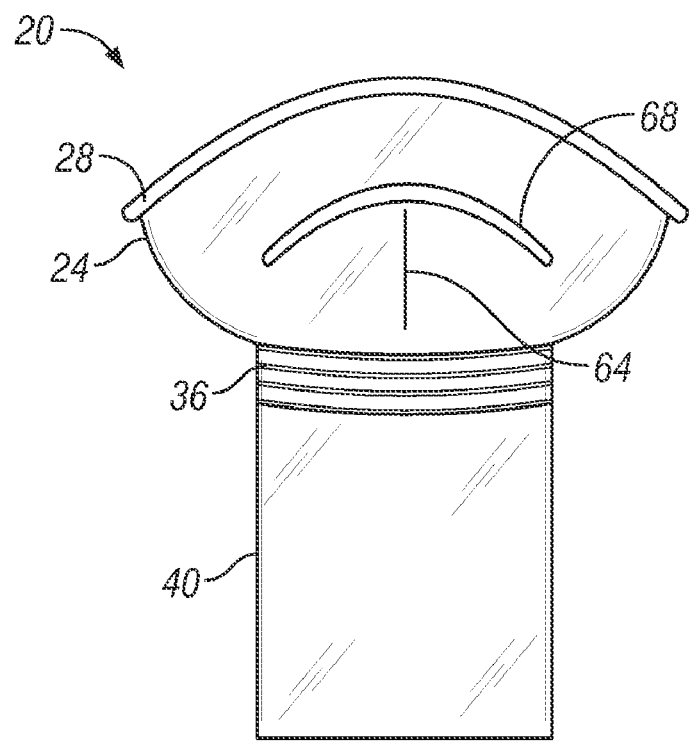
FIG. 1 is an elevational front view of a urine specimen collection device in accordance with the present invention
Figure 2:
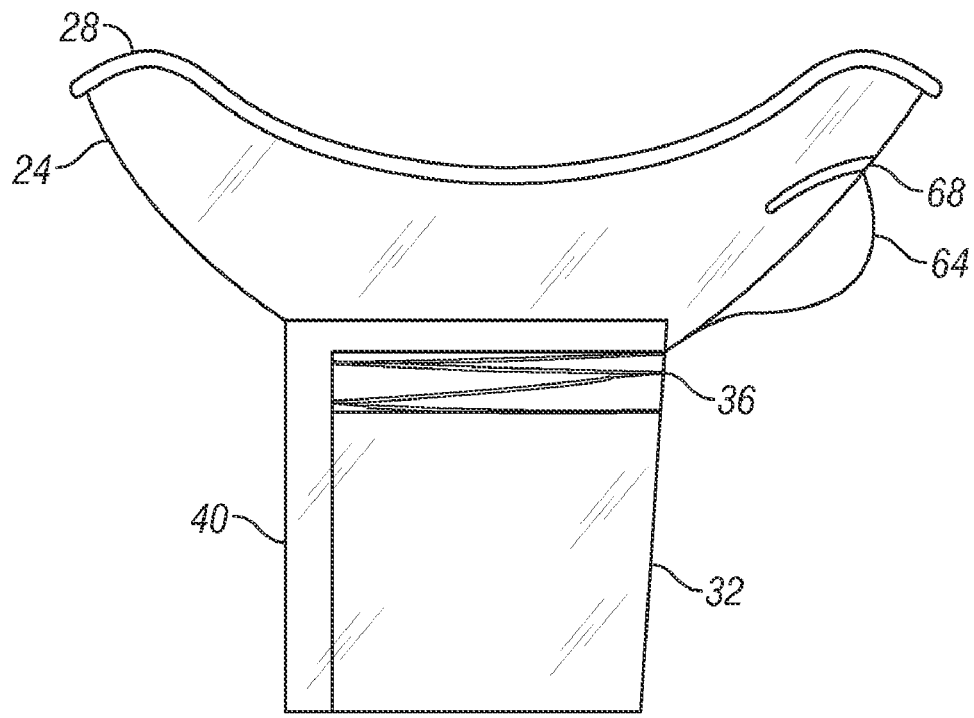
FIG. 2 is an elevational side view of a urine specimen collection device of FIG. 1.

There is provided a urine specimen collection device. The device includes a body adapted to support a specimen collector. The device includes a pull tab movably connected to the body, the pull tab being movable between a first position and a second position. The urine selectively flows through the body and into the specimen collector when the pull tab is generally positioned in the second position and urine flows through the body and into a diverter tube when the pull tab is generally positioned in the first position.

DETAILED DESCRIPTION OF THE INVENTION

This application claims the benefit of U.S. Provisional Application No. 60/766,577, filed Jan. 24, 2006.

Preliminarily, it should be noted that certain terms used herein, such as for example upper and lower are used to facilitate the description of the invention. Unless otherwise specified or made apparent by the context of the discussion, such terms and other directional terms should be interpreted with reference to the figure(s) under discussion. Such terms are not intended as a limitation on the position in which the invention or components may be used. Indeed, it is contemplated that the components of the invention may be easily positioned in any desired orientation for use. Likewise, numerical terms such as for example "first", and "second" are not intended as a limitation or to imply a sequence, unless otherwise specified or made apparent by the context of the discussion. The term "operatively connected" is understood to include a linking together of the portions under consideration and may include a physical engagement and/or a functional or operational connection.

Referring now to the drawings, there is illustrated in FIGS. 1 through 6 a urine specimen collection device, indicated generally at 20, according to the invention. The device 20 is desirable for collecting urine, including but not limited to urine from "mid-stream" collection. When a user (not shown) provides a urine specimen, the first urine that passes from the body has characteristics which are undesirable for some types of laboratory analysis. For this reason, it is desirable to have a device which is adapted to selectively discard the first urine portion that passes, yet collect urine from "mid-stream" of the flow of urine. The device 20 is described in association with the mid-stream collection of urine, but may have other valuable uses as well.

The illustrated device 20 includes a body 24. The body 24 and other components of the device 20 may be made of any suitable material and by any suitable method. Since sanitary concerns may be important in use of the device 20, materials that lend themselves to being disposable may be considered. The body 24 may be generally concave. The term "concave" may include [but is not limited to] structures or components that are generally curved generally inward—and may be generally like the inner surface of a bowl or sphere. The illustrated body 24 includes a generally concave interior surface.

The body 24 may include a rolled edge 28. The rolled edge 28 may be contoured and adapted so that the device 20 is readily positionable against and/or adjacent to the user's pubic region and or legs. The term "adjacent" may include [but is not limited to] structures or components situated generally near or generally close to each other, which may or may not be touching and/or connected. If the rolled edge 28 employed is unnecessarily jagged or sharp, the user may be exposed to a hazard in positioning the device 20 against and/or adjacent to the user's body for urine collection. The rolled edge 28 is shown positioned at the upper ridge of the body 24. The rolled edge 28 may be a generally rounded edge, as shown.

Figure 3:
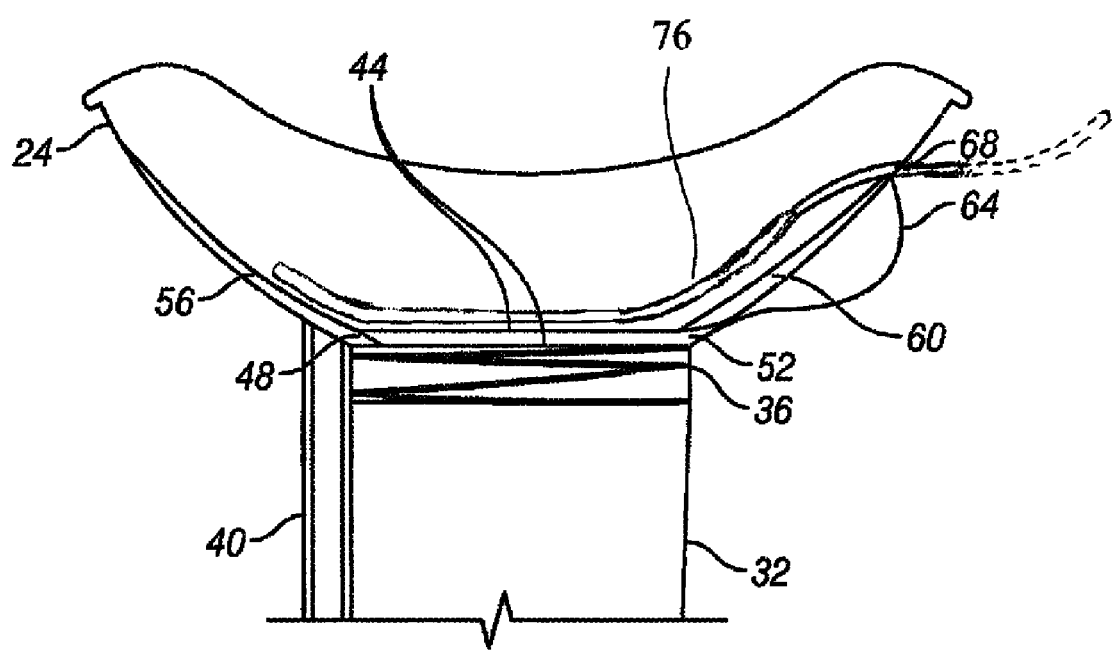
FIG. 3 is a cross sectional view in elevation of the urine specimen collection device of FIG. 1.

Referring now primarily to FIG. 3, the body 24 may be adapted to support a specimen collector 32. The term "support" may include (but is not limited to) one or more structures or components adapted to generally hold up, serve as a foundation for, and/or prop up something. The body 24 shown removable secured to the specimen collector 32. The illustrated specimen collector 32 is operatively connected to a threaded collar 36. The term "collar" as used in this application may be understood to include, but is not limited to, any structure or functionality which is generally ring-shaped and guides, seats, or restricts another mechanical part. The illustrated threaded collar 36 is shown as including a female adaptor. The illustrated specimen collector 32 is shown to include a male adaptor. The specimen collector 32 may be operatively connected to the body 24 in any suitable fashion any may employ any suitable means of coupling. The term "coupling" as used in this application may be understood to include [but is not limited to] one or more structures or components that join two things, including a device for connecting two things and/or objects.

A urine discharge tube 40 is shown secured to the body 24. The discharge tube 40 may be selectively employed as a diverter tube. The term "tube" may include (but is not limited to) any structure or functionality which may used to transport a fluid, such as for example, urine. The term "fluid" may include (but is not limited to) a substance having particles that easily move and change their relative position generally without a separation of the mass and that generally easily yield to pressure. It will be appreciated that fluids are generally capable of flowing. Nonlimiting examples of fluids include liquids and gases, including urine, water, air, hydraulic fluids, and the like. A substance may be considered a fluid even though solid particles are entrained therein.

The urine discharge tube 40 is selectively in fluid communication with the body 24. The term "fluid communication"

may suggest a route and/or system of routes for the flow of a fluid. The term "fluid communication" may also suggest the traveling and/or transporting of a fluid. The term "fluid communication" may include [but is not limited to] the general ability or capacity for fluid to flow between the parts, sections, or components under consideration.

The illustrated body 24 includes a track 44. The term "track" as used in this application may be understood to include [but is not limited to] any structure or functionality which provides a path or pathway for the movement of some object. The term "track" as used in this application may be understood to include a rail or a pair of generally parallel rails on which some object selectively may move.

A first track guide 48 and a second track guide 52 may be provided in conjunction with a first pocket 56 and a second pocket 60. The first track guide 48 and the first pocket 56 are shown generally adjacent to the discharge tube 40. The second track guide 52 and the second pocket 60 are shown at the end of the body 24 wherein a handle 64 may be positioned. A slot 68 in the body 24 may be positioned adjacent to the handle 64—at any other suitable location. The term "slot" as used in this application may be understood to include, but is not limited to, any structure or functionality which defines an opening into which something can be inserted. The illustrated slot is generally curved, though may assume any suitable shape and/or contour. A pull tab 76 may be movable between at least first and second positions (the second position shown in ghost), and create a valve in association with an opening in the body 24.

Figure 4:
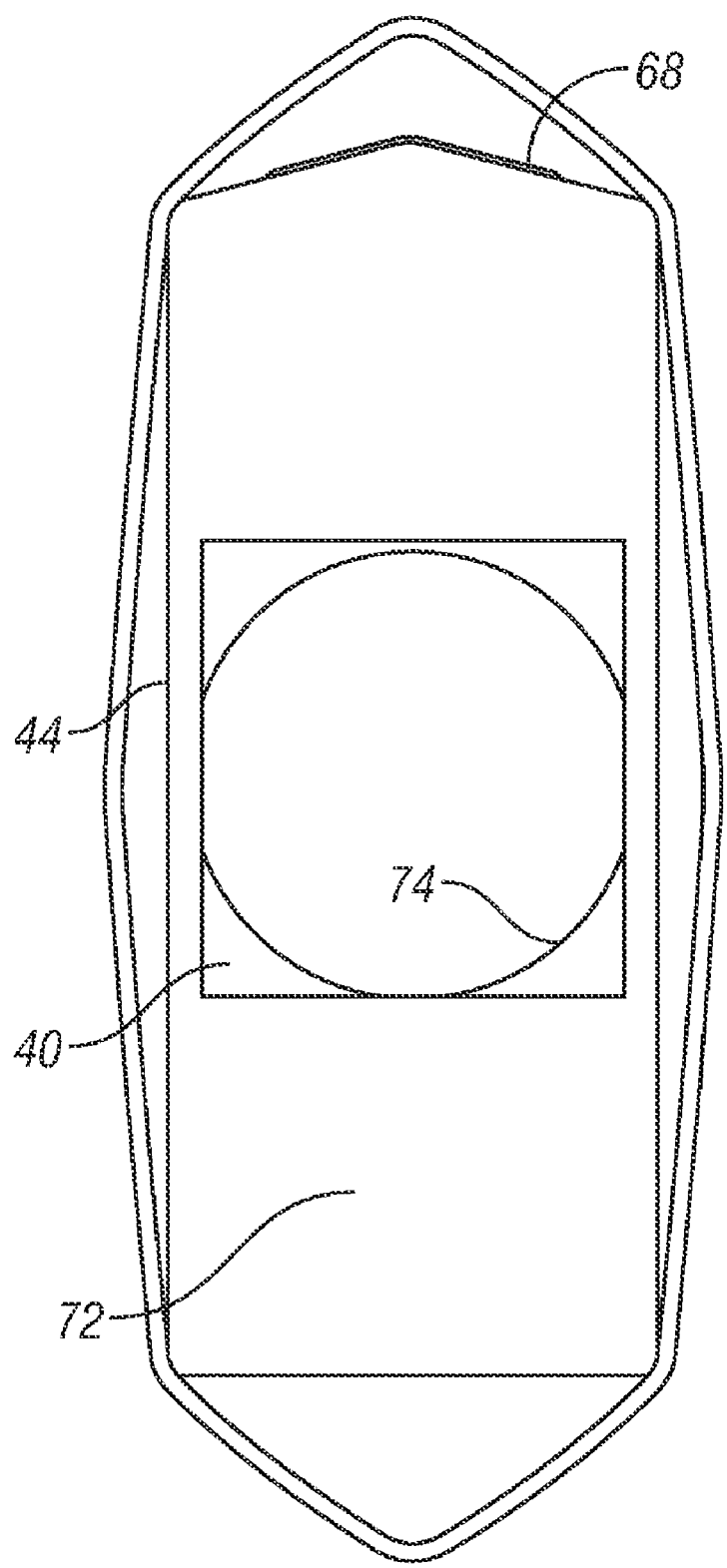
FIG. 4 is a top plan view in elevation of the urine specimen collection device of FIG. 1.

Referring now primarily to FIG. 4, a cover 72 may be employed in conjunction with the body 24—or may be integrally formed with the body 24. It will be noted that the illustrated cover 72 does not occlude an opening 74 that is defined in the body 24 that allows for fluid communication between the body 24 and the specimen collector 32. It will be noted that the illustrated cover 72 does not occlude the discharge tube 40. The cover 72 may be generally concave to coincide with the contour of the body 24. The cover 72 may be operatively connected to the body 24.

Figure 5:
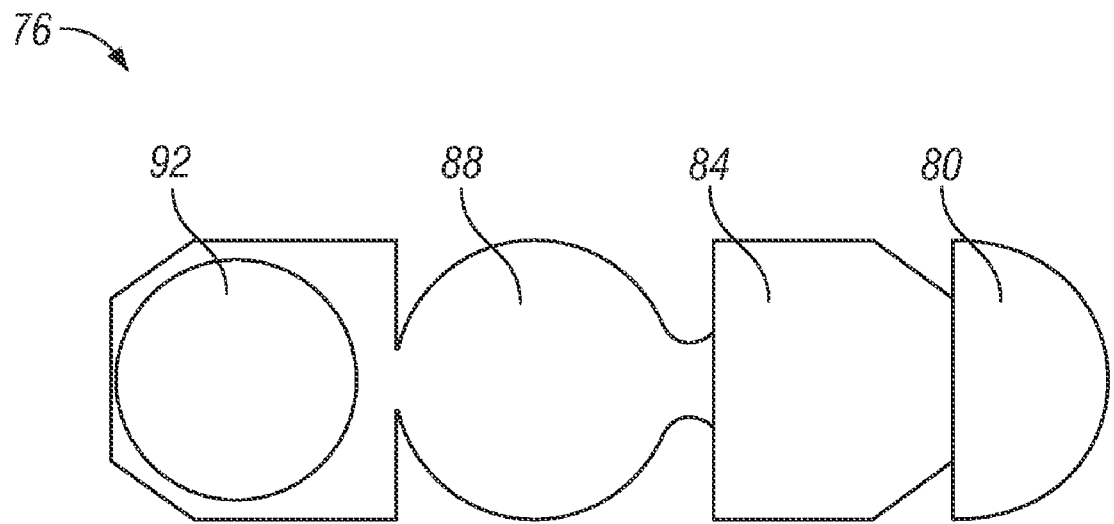
FIG. 5 is a top plan view in elevation of a pull tab for the urine specimen collection device of FIG. 1.
Figure 6:
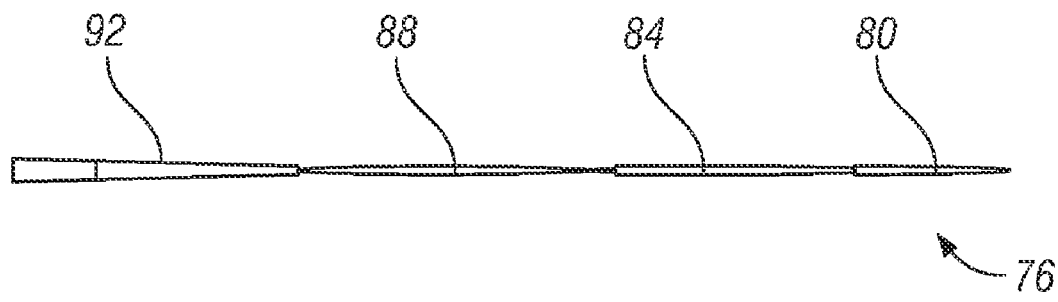
FIG. 6 is an elevational side view of the pull tab for the urine specimen collection device of FIG. 1.

Referring now primarily to FIG. 5 and FIG. 6, a pull tab 76 may be used in conjunction with the body 24 of the device 20. The illustrated pull tab 76 includes a handle portion 80, a connector portion 84, a collar cover 88, and a ring portion 92. The pull tab 76 is desirable to insert into the slot 68 of the device 20. When the pull tab 76 is inserted into the slot 68, the handle portion 80, or some portion of the handle portion 80, protrudes from the slot 68 of the device 20. It will be noted that the ring portion 92 is generally wedge-shaped as shown in FIG. 6. The term "wedge" as used in this application may be understood to include (but is not limited to) any structure or functionality which is generally thicker at one end and generally thinner at the other end. The term "wedge" may be also understood to include (but is not limited to) any structure or functionality which generally tapers from the thicker end to the thinner end.

The pull tab 76 is generally selectively movable between an open position and a closed position. Depending on how the pull tab 76 is positioned, it may be partially open and/or partially closed. When the pull tab 76 is in the closed position, the urine flow is diverted into the discharge tube 40. When the pull tab 76 is in the open position, the urine is permitted to flow into the specimen collector 32. When the user properly synchronizes urination with the positioning of the pull tab 76, the urine which is permitted to flow into the specimen collector 32 is from a "midstream" urine stream.

The pull tab 76 and the opening 74 generally function as a valve. The term "valve" as used in this application may be understood to include [but is not limited to] any structure or functionality which controls and/or moderates the passage and/or flow of fluid. Control of the flow of fluid is by means of a movable element that opens, shuts, or partially obstructs an opening in a passageway. Control of the flow of fluid for the urine specimen collection device is facilitated by the pull tab 76. It should be noted that the respective positions of the discharge tube 40 and the opening 74 may be reconfigured as desired to produce alternate embodiments When the pull tab 76 is in the closed position, the ring portion 92 is generally located in the first pocket 56. The pull tab 76 is selectively moveable along the track 44. The pull tab 76 may be moved from the closed position to the open position by the user, or some other person or other pulling means, pulling generally laterally on the handle portion 80 of the pull tab 76. When the pull tab 76 is in the open position, the ring portion 92 is generally located above the opening 74 that is defined in the body 24 that allows for fluid communication between the body 24 and the specimen collector 32.

Figure 7:
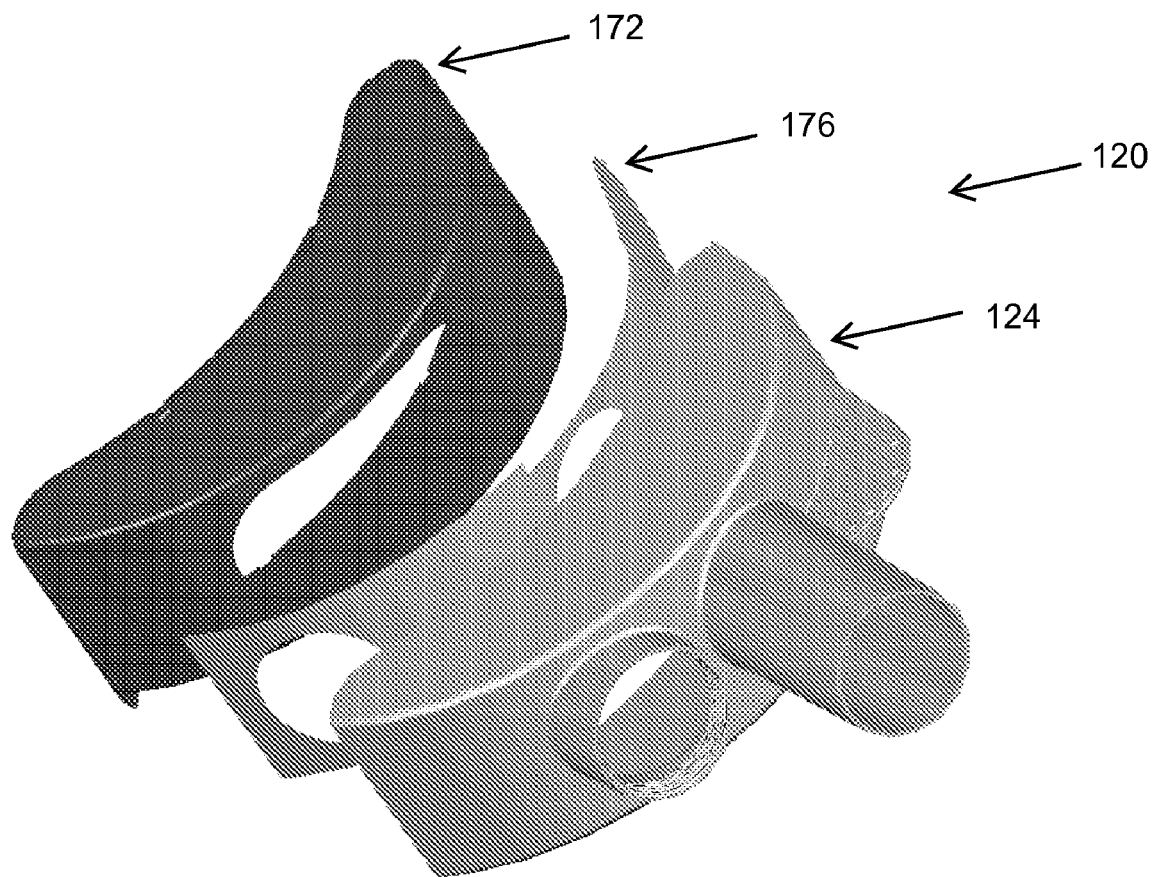
FIG. 7 is a perspective view of an alternate embodiment of the urine specimen collection device.

Alternate embodiments may be employed to practice the invention. One such alternate embodiment may be viewed in FIG. 7. The device 120 includes a body 124, a pull tab 176, and a cover 172. The device 120 functions analogously to the device 20 discussed and disclosed herein in FIGS. 1-6. It will be noted that the pull tab 176 includes two openings.

The invention may be made from any suitable material and by any suitable method. The invention may be adapted to fit a wide variety of uses. It will be appreciated that the components of the invention may be easily modified as needed to accommodate varying sizes and shapes. These definitions in this application are provided solely to facilitate an understanding of the invention—not to limit the invention.

It is to be understood that the invention is not limited in its application to the details of construction and to the arrangements of the components set forth in the accompanying description or illustrated in the drawings. The invention is capable of other embodiments and of being practiced and carried out in various ways. Also, it is to be understood that the phraseology and terminology employed herein are for the purpose of description and should not be regarded as limiting. The disclosure may readily be utilized as a basis for the designing of other structures, methods and systems for carrying out the present invention. It is important, therefore, that the claims be regarded as including equivalent constructions. Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract and disclosure are neither intended to define the invention of the application, which is measured by the claims, nor are they intended to be limiting as to the scope of the invention in any way.

What is claimed is:
1. A urine specimen collection device comprising:
a body having an open cavity and a top portion with a concave shape, wherein the body includes an opening and removably supports a specimen collector,
a pull tab having at least one opening in a pull tab body movably connected to the body, the pull tab being movable between at least a first position and a second position, wherein urine can selectively flow through the body and the at least one opening of the pull tab body and into the specimen collector when the pull tab is generally positioned in the second position and urine can selec- tively flow through the body and be evacuated from the device when the pull tab is generally positioned in the first position, and a detachable cover associated with the body, wherein the cover includes a hole that cooperates with the pull tab to selectively direct urine to the specimen collector or to evacuate urine from the body.

2. The device of claim 1 further comprising a track in the body wherein the pull tab is moveably connected to a track in the body.

3. The device of claim 2 wherein the body includes a concave interior surface.

4. The device of claim 1 wherein the pull tab may be inserted into the body through a slot in the body.

5. The device of claim 1 wherein the pull tab has a portion thereof which is wedge shaped to position the opening in the pull tab body adjacent the opening in the body.

6. The device of claim 1 further comprising a coupling to secure the specimen collector to the body.

7. The device of claim 1 wherein the pull tab selectively covers the opening to selectively control flow of urine through the opening in the body.

8. A urine specimen collection device comprising:
a body having a cavity and an opening on the bottom, the body supporting a specimen collector adjacent the opening,
a valve defined by the opening in the body and a pull tab having an opening in a pull tab body, and
a cover associated with the body which does not occlude the opening in the body, wherein the cover and the body define a track for movement of the pull tab within the track, wherein the valve selectively opens and closes, by the pull tab, to allow urine to flow through the valve into the specimen collector when the valve is selectively open, and urine to be evacuated from the body when the valve is selectively closed.

9. The device of claim 8 wherein the pull tab has a portion thereof which is wedge shaped to position the opening in the pull tab body adjacent the opening in the body.

10. The device of claim 8 wherein the pull tab includes a ring portion and a cover portion.

11. A urine specimen collection device comprising:
a body having an open cavity and having a top portion with a concave shape for positioning adjacent at least one of a user's pubic region and legs, wherein the body is operatively connectable to a specimen collector,
a movable pull tab having an opening in a pull tab body, wherein the body and the opening of the pull tab body is in fluid communication with a discharge opening when the pull tab is generally positioned in a first position and the body is in fluid communication with the specimen collector when the pull tab is generally positioned in a second position.

12. The device of claim 11 wherein the pull tab includes a portion thereof which is wedge shaped to position the opening in the pull tab adjacent the opening in the body.

13. The device of claim 11 wherein the pull tab may be inserted into the body through a slot in the body.

14. The device of claim 11 wherein the pull tab includes a ring portion and a cover portion.

15. The device of claim 11 wherein a portion of the pull tab is generally wedge-shaped to position the opening in the pull tab adjacent the opening in the body.

\* \* \* \* \*